(12) United States Patent
Ueno

(10) Patent No.: US 6,197,821 B1
(45) Date of Patent: Mar. 6, 2001

(54) ENDOTHELIN ANTAGONIST

(75) Inventor: Ryuji Ueno, Montgomery, MD (US)

(73) Assignee: R-Tech Ueno, Ltd., Osaka (JP)

(*) Notice: Subject to any disclaimer, the term of this patent is extended or adjusted under 35 U.S.C. 154(b) by 0 days.

(21) Appl. No.: 09/355,270

(22) PCT Filed: Nov. 16, 1998

(86) PCT No.: PCT/JP98/05143

§ 371 Date: Jul. 27, 1999

§ 102(e) Date: Jul. 27, 1999

(87) PCT Pub. No.: WO99/27934

PCT Pub. Date: Jun. 10, 1999

(30) Foreign Application Priority Data

Nov. 28, 1997 (JP) .................................................. 9-327832

(51) Int. Cl.⁷ .................... A61K 31/5575; A61K 31/559
(52) U.S. Cl. ............................................................. 514/573
(58) Field of Search .............................................. 514/573

(56) References Cited

U.S. PATENT DOCUMENTS

| | | | |
|---|---|---|---|
| 3,853,951 | 12/1974 | Bernady et al. | 260/468 D |
| 3,981,868 | 9/1976 | Bernady et al. | 260/240 J |
| 4,018,811 | 4/1977 | Schaub et al. | 260/468 K |
| 5,212,324 | 5/1993 | Ueno | 554/118 |
| 5,252,605 | 10/1993 | Ueno | 514/573 |
| 5,346,921 | 9/1994 | Ueno | 514/573 |
| 5,362,751 | 11/1994 | Ueno | 514/530 |

FOREIGN PATENT DOCUMENTS

| | | | |
|---|---|---|---|
| 0284180 | * | 9/1988 | (EP) . |
| 0-343904A1 | | 11/1989 | (EP) . |
| 0 857718A1 | | 8/1998 | (EP) . |
| 10-7574A | | 1/1998 | (JP) . |

OTHER PUBLICATIONS

Tolstikov, GA, Prostanoids. XXX. Synthesis of 11–desoxyprostaglandin E and F analogs., Zh. Org. Khim., vol. 26, No. 1 (1990) p. 119–127.

Abstract of JP 2–32021 published Feb. 1, 1990.

Fukuda et al., The Journal of Pharmacology and Experimental Therapeutics, vol. 260, No. 3, 1128 (1992).

\* cited by examiner

*Primary Examiner*—Phyllis G. Spivack
(74) *Attorney, Agent, or Firm*—Sughrue, Mion, Zinn, Macpeak & Seas, PLLC

(57) ABSTRACT

The present invention provides an antagonist for endothelin which is considered to have a relation to hypertension, Buerger is disease, asthma, eyegrounds diseases, and the like. Said endothelin antagonist contains 15-keto-prostaglandin E compounds, especially 13,14-dihydro-15-keto-16-mono or dihalo-prostaglandins.

14 Claims, No Drawings

ENDOTHELIN ANTAGONIST

TECHNICAL FIELD

The present invention relates to a new use of 15-keto-prostaglandin E compounds as an endothelin antagonist.

BACKGROUND ART

Endothelin is an endogenous bioactive peptide composed of 21 amino acids, and three types of which, i.e., endothelin-1, endothelin-2, and endothelin-3 are known.

Endothelin is a bioactive substance for continuously constricting vascular or non-vascular smooth muscle in direct or indirect way (regulation of release of a variety of endogenous substances), and production of endothelin increases due to lesion of endothelium. Excessive production of endothelin is considered to be a cause for diseases such as hypertension, pulmonary hypertension, Buerger disease, Raynaud disease, asthma, eyegrounds—amphiblestrodes, chorioidea, and the like—diseases, diabetes, arterial sclerosis, renal failure, cardiac infarction, angina pectoris, cerebrovascular contraction, and cerebral infarction. Furthermore, it is known that endothelin is an important mediator with respect to multiple organ failures, and diseases such as disseminated intravascular coagulation due to endotoxin shock and the like as well as renal lesion induced by cyclosporin and the like. Moreover, it is also known that an endothelin concentration in blood increases after organ transplantation such as liver transplant.

Prostaglandins (Prostaglandin is referred to as PG hereinafter) are a group of organic carboxylic acids contained in a tissue or an organ of human beings or mammals and having a wide range physiological activity. The PGs existing in nature have a prostanoic acid backbone represented by formula (A) as a general structure:

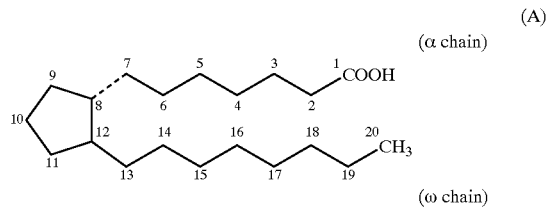

On the other hand some of synthetic analogs have a modified structure.

Natural PG groups are classified based on the structural feature of five-membered ring into PGA group, PGB group, PGC group, PGD group, PGE group, PGF group, PGG group, PGH group, PGI group, and PGJ group; and further they are classified as follows on the basis of presence or absence of unsaturation and oxidation at their chain portions:

numerical subscript 1 . . . 13,14-unsaturated-15-OH numerical subscript 2 . . . 5,6- and 13,14-di-unsaturated-15-OH numerical subscript 3 . . . 5,6-, 13,14- and 17,18-ti-unsaturated-15-OH Moreover, the PGF group is classified into α- (the hydroxy group is in an alpha-configuration) and β- (the hydroxy group is in a beta-configuration) based on the configuration of the hydroxy group at the 9-position.

It has been known that $PGE_1$, $PGE_2$ and $PGE_3$ have an activity of vasodilation, blood depression, reduce of gastric juice, increase of intestine movement, uterine contraction, diuresis, bronchodilation and antiulcer. It has been also known that $PGF_1\alpha$, $PGF_2\alpha$ and $PGF_3\alpha$ have an activity of hypertension, vasoconstriction, increase of intestine movement, uterine contraction, involution of corpus luteum and tracheo contraction.

Further, some of 15-keto-PGs (i.e., PGs having an oxo group instead of a hydroxyl group at the 15-position) and 13,14-dihydro-15-keto-PGs are compounds naturally produced by the enzymatic action during metabolism (Acta Physiologica Scandinavica, Vol. 66, 509(1966)). It was reported that 15-keto-$PGF_2$a has an activity of antipregnancy. Further, it was known that 15-keto-PGE compounds could be used for the treatment of various kinds of diseases (EP Patent Application No. 0 284 180 A).

As an action against endothelin it has been known that $PGE_2$ inhibits vasoconstriction of a rat which is induced by the endothelin. This inventor has reported that prostanoic acid compounds whose hydrocarbon backbone is extended in α-chain have a strong endothelin antagonistic activity (WO 97/47595) and a 15-keto-prostaglandin F compound expresses endothelin antagonistic activity by an eye-administration (Japanese Patent Application KOKAI No. Hei. 10-007574). It, however, has not been known that 15-keto-prostaglandin E compounds (excepting compounds having 8 or more carbon atoms in the α-chain backbone) have an endothelin antagonistic effect.

The Most Preferable Embodiment for Working the Invention

The purpose of the invention is to provide an endothelin antagonist useful for the treatment of various kinds of disease and pathology participated of endothelin. Further the present invention relates to a treatment of disease caused by the excessive production of endothelin and a use of 15-keto-prostaglandin E compounds for manufacturing the endothelin antagonist.

As the result of research of biological activity of 15-keto-PGE compounds, it has been found that 15-keto-PGE compounds exhibit an extremely strong endothelin antagonistic effect. That is, the present invention provides an endothelin antagonist which comprises 15-keto-prostaglandin E compounds as an effective compound excepting prostanoic acids having 8 or more carbon atoms in the α-chain.

As the endothelin antagonist of the present invention has an extremely strong endothelin antagonistic activity, it is effective for the treatment of various kinds of disease and pathology related to by the endothelin. The term "treatment" in the present specification includes any kinds of control of disease such as prevention, cure, decrudescence, reduction of symptom, quit of progression and the like.

In the present invention, "15-keto-prostaglandin E compounds" (referred to as 15-kto-PGE compounds hereinafter) include any substituention products or derivatives having an oxo group at the 15-position of the backbone of prostanoic acid instead of a hydroxyl group, irrespective to the number of double bond, presence or absence of a substituent or modification on the α-chain or ω-chain (excepting compounds having 8 or more carbon atoms on the backbone of the α-chain).

Nomenclature of 15-keto-PGE compounds in the present invention herein uses the numbering system of prostanoic acid represented in formula (A) shown above.

While formula (A) shows a basic skeleton having twenty carbon atoms, the carbon atoms in the present invention are not limited thereto . Namely, the numbers of the carbons constituting the basic skeleton are assigned in such that number 1 is assigned to carboxylic acid, numbers 2 to 7 are given to the carbons on the α-chain in accordance with the order directing to the five-membered ring, numbers 8 to 12 are assigned to the carbons of the five-membered ring, and numbers 13 to 20 are given to the carbons on the ω-chain, respectively. However, in the case where carbon atoms decrease on the α-chain, numbers are successively deleted from the 2-position. Likewise, in case of decreasing carbon atoms on the ω-chain, the number of carbon atoms is successively deleted from 20-position, while in case of increasing carbon atoms on the ω-chain, nomenclature is made in such that the carbon atoms at the 21-position and thereafter positions are considered to be substituents. Further, with respect to steric configuration, it is in accordance with that involved in the above indicated basic skeleton unless otherwise specified.

Therefore, 15-keto-PGE compounds having 10 carbon atoms in the ω-chain is named as 15-keto-20-ethyl-PGE compounds (excepting compounds having 8 or more backbone carbon atoms in the α-chain from the present invention).

The above Formula shows a specific configuration which is the most typical one, but any compounds, otherwise specifically illustrated, have this configuration in this specification.

PGEs generally mean prostanoic acids having an oxo group at the 9-position and a hydroxyl group at the 11-position, but in the present invention 15-keto-prostaglandin E compounds include a compound having another group at the 11-position instead of the hydroxyl group. In this case these compounds are named in the form of "11-dehydorxy-11-substituents". The compounds having a hydrogen atom instead of the hydroxyl group at the 11-position are simply called as 11-dehydroxy compounds.

15-Keto-PGE compounds of the present invention include any PGE derivatives which have an oxo group at the 15-position instead of the hydroxyl group, and seven or less carbon atoms in α-chain backbone, and may have one double bond between the 13- and 14-positions (15-keto-PGE type 1 compounds), in addition thereto one double bond between the 5- and 6-positions (15-keto-PGE type 2 compounds), and further two double bonds between the 5- and 6-positions and the 17- and 18-positions (15-keto-PGE type 3 compounds).

Further, 15-keto-PGE compounds include compounds saturated at the 13-14 position, that is, 13,14-dihydro-15-keto-PGE compounds.

Typical examples usable in the present invention are 15-keto-PGE type 1, 15-keto-PGE type 2, 15-keto-PGE type 3, derivatives thereof and the like.

Examples of the substitutes or derivatives are compounds in which the carboxyl group at the terminal position of α-chain of 15-keto-PGEs is esterified, physiologically acceptable salts, the bond between the 2- and 3-positions is a double bond or the bond between the 5- and 6-positions is a triple bond; compounds having a substituent(s) at the 3-, 5-, 6-, 16-, 17-, 18-, 19- and/or 20-position; compounds having a lower alkyl group, a hydroxy lower alkyl group or a hydrogen atom instead of the hydroxyl group at the 11-position.

In the present invention substituents which may bond the carbon atom at 3-, 17-, 18- and/or 19-position may be, for example, a $C_{1-4}$ alkyl group, especially methyl or ethyl. Substituents at 16-position include, for example, a lower alkyl group such as a methyl group, an ethyl group and the like, a hydroxyl group, a halogen atom such as a chlorine atom, a fluorine atom and the like, an aryloxy group such as a trifluoromethylphenoxy group. Substituents at the 17-position a hologen atom such as a chlorine atom, a fluorine atom and the like. Substituents at the 20-position may be saturated or unsaturated lower alkyl such as $C_{1-4}$ alkyl, lower alkoxy such as $C_{1-4}$ alkoxy, lower alkoxyalkyl such as $C_{1-4}$ alkoxy-$C_{1-4}$ alkyl. Substituents at the 5-position may include a halogen atom such as a chlorine atom, a fluorine atom and the like. Substituents at the 6-position may include an oxo group forming a carbonyl group. When the carbon atom at the 11-position has a hydroxyl group, a lower alkyl group or a lower (hydroxy) alkyl group as a substituent, the steric configuration of these group may be α, β or a mixture thereof.

Further, the above derivatives may be compounds having substituents such as an alkoxy group, a phenoxy group, a phenyl group and the like at the terminal position of the ω-chain in compounds having an ω-chain shorter than that of natural PGs.

Preferable compounds are ones having a lower alkyl group such as a methyl group, an ethyl group and the like, a halogen atom such as chlorine, fluorine and the like at the 16-position; ones having a lower alkyl group such as methyl, ethyl and the like, and/or a halogen atom such as chlorine, fluorine and the like at the 17-position;

compounds having a lower alkyl group such as methyl, ethyl and the like at the 18- or 19-position; compounds having an halogen atom such as chlorine, fluorine and the like at the 5-position; compounds having an oxo group at the 6-position, compounds having a lower alkyl group such as methyl, ethyl and the like at the 20-position; compounds having a phenyl group or a phenoxy group which may be substituted with a halogen atom or a halogenated alkyl group instead of the alkyl chain on and after the carbon atom of the 16- or 17-position.

13, 14-Dihydro-15-keto-PGE compounds whose 13-14 carbon bond is a single bond, compounds having one or two halogen atoms such as a chlorine atom, a fluorine atom and the like at the 16-position (15-keto-16-mono- or dihalogen-PGE compounds) are exemplified as the most preferable compounds.

Preferable compounds used in the present invention are represented by following Formula (I):

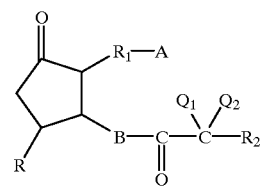

(I)

wherein R is a hydrogen atom, a hydroxyl group, a hydroxy (lower)alkyl group or a lower alkyl group, A is —CH$_2$OH, —COCH$_2$OH, —COOH or functional derivatives thereof, B is —CH$_2$—CH$_2$—, —CH=CH—, —C—C—

$Q_1$ and $Q_2$ are a hydrogen atom, a halogen atom or a lower alkyl group, $R_1$ is a bivalent saturated or unsaturated $C_2$–$C_6$ hydrocarbon residue which is unsubstituted or substituted with halogen, oxo or aryl, $R_2$ is a saturated or unsaturated, lower to medium aliphatic hydrocarbon residue which is unsubstituted or substituted with halogen, oxo, hydroxyl, lower alkoxy, lower alkanoyloxy, lower cycloalkyl, aryl or aryloxy; a lower cycloalkyl group; an aryl group or an aryloxy group.

In the above Formula the term "unsaturated" in the definition of $R_1$ and $R_2$ means that one or more double bonds and/or triple bonds are contained isolatedly, separately or continually as a carbon-carbon bond in a main chain or a side chain. According to a usual nomenclature, the position of the unsaturated bond between two continued positions is represented by the young position number, and the unsaturated bonds between two discontinued positions are represented by the both position numbers. Preferable unsaturated bonds are a double bond at the 2-position and a double bond or a triple bond at the 5-position.

The term "lower-medium aliphatic hydrocarbon" means a hydrocarbon having a straight or side chain of 1 to 14 carbon atoms (wherein the side chain has preferably 1 to 3 carbon atoms), and preferably, 2 to 10 carbon atoms.

The term "halogen" includes fluorine, chlorine, bromine and iodine.

The term "lower" means a group having 1 to 6 carbon atoms unless otherwise specified.

The term "lower alkyl" means a straight- or branched saturated hydrocarbon group having 1 to 6 carbon atoms, for example, methyl, ethyl, propyl, isopropyl, butyl, isobutyl, t-butyl, pentyl, and hexyl.

The term "lower alkoxy" means a lower alkyl-O- wherein the lower alkyl is as described above.

The term "hydroxy(lower)alkyl" means an alkyl as described above, which is substituted by at least one hydroxy group, for example, hydroxymethyl, 1-hydroxyethyl, 2-hydroxyethyl, and 1-methyl-1-hydroxyethyl.

The term "lower alkanoyloxy" means a group represented by the formula RCO-O- wherein RCO- is an acyl formed by oxidation of a lower alkyl as described above, for example, acetyl.

The term "lower cycloalkyl group" means a group formed by cyclization of a lower alkyl group containing 3 or more carbon atoms as described above, for example, cyclopropyl, cyclobutyl, cyclopentyl, and cyclohexyl.

The term "aryl" includes aromatic hydrocarbon rings or heterocyclic groups (preferably monocyclic groups) which may be substituted, for example, phenyl, tolyl, xylyl, and thienyl. An example of the substituent in this case includes halogen, and halogen substituted lower alkyl group (wherein halogen atom and lower alkyl group are as described above).

The term "aryloxy" means a group represented by the formula ArO- (wherein Ar is an aryl group as described above).

The term "functional derivatives" of the carboxy group represented by A includes salts (preferably pharmaceutically acceptable salts), esters, and amides.

Examples of suitable "pharmaceutically acceptable salts" include nontoxic salts which are commonly used, and they are salts with inorganic bases, for example, alkali metal salts (sodium salt, potassium salt and the like); alkaline earth salts (calcium salt, magnesium salt and the like); ammonium salts; salts with organic bases, for example, amine salts (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, lysine salt, procaine salt, and caffeine salt); basic amino acid salts (such as arginine salt, and lysine salt); tetraalkyl ammonium salts and the like. These salts may be manufactured from, for example, corresponding acids and bases in accordance with a conventional manner or salt exchange.

The esters includes aliphatic esters, for example, lower alkyl esters such as methyl ester, ethyl ester, propyl ester, isopropyl ester, butyl ester, isobutyl ester, t-butyl ester, pentyl ester, and 1-cyclopropylethyl ester; lower alkenyl esters such as vinyl ester, and allyl ester; lower alkynyl esters such as ethynyl ester, and propynyl ester; hydroxy (lower)alkyl esters such as hydroxyethyl ester; and lower alkoxy(lower)alkyl esters such as methoxymethyl ester, and 1-methoxyethyl ester as well as, for example, optionally substituted aryl esters such as phenyl ester, tosyl ester, t-butylphenyl ester, salicyl ester, 3,4-dimethoxyphenyl ester, and benzamidephenyl ester; and aryl(lower)alkyl esters such as benzyl ester, trityl ester, and benzhydryl ester. An example of amides includes mono- or di-lower alkyl amides such as methylamide, ethylamide, and dimethylamide; aryl amides such as anilide, and toluidide; and alkyl or aryl sulfonyl amides such as methylsulfonyl amide, ethylsulfonyl amide, and tolylsulfonyl amide.

Examples of preferable R are hydrogen or hydroxyl, and most preferably hydroxyl.

Examples of preferable A are —COOH, physiologically acceptable salts, esters or amides.

Example of preferable B is —$CH_2$—$CH_2$—, that is, one having a structure constituting 13,14-dihydro type.

Examples of preferable $Q_1$ and $Q_2$ are at least one being halogen, and preferably both being halogen. Most preferable one is fluorine, that is, 16,16-difluoro type.

Example of preferable $R_1$ is a $C_4$–$C_6$ hydrocarbon, and most preferable one is a $C_6$ hydrocarbon.

Example of preferable $R_2$ is a $C_1$–$C_{10}$ hydrocarbon, and most preferably a $C_2$–$C_8$ hydrocarbon, especially having one or two $C_1$-branches.

In the above Formula (I), the configuration of the ring, α- and/or ω-chain may be the same as or different from that of a natural prostaglandin. The present invention, however, includes a mixture of compounds having a configuration of natural prostaglandins and compounds having a configuration of non-natural prostaglandins.

Examples of typical compounds of the present invention are 13,14-dihydro-15-keto-16-mono- or di-fluoro-PGE compounds and derivatives thereof. As the derivatives there are exemplified 6-oxo derivatives, $\Delta^2$-derivatives, 3-methyl derivatives, 6-keto derivatives, 5-fluoro derivatives, 5,5-difluoro derivatives, 17-methyl derivatives, 18-methyl derivatives, 19-methyl derivatives, 20-methyl derivatives, 20-ethyl derivatives, 19-desmethyl derivatives and 17-torinor-17-phenyl derivatives.

In the 15-keto-PGE compounds used in the present invention, when 13-,14-positions are saturated and 15-position is oxo (i.e., in case of 13,14-dihydro-15-keto-form), there is a case where keto-hemiacetal equilibrium occurs as a result of formation of hemiacetal between the hydroxy at 11-position and the keto at 15-position.

In the case when such tautomers exist, a ratio of existence of both the tautomers are depend upon the structure of the other party or the types of substituents, and according to circumstances, either of tautomers exists predominantly. However, the present invention includes these both tautomers, and there is a case where a compound is indicated in accordance with either keto-form structural formula or nomenclature irrespective of presence or absence of such tautomers. In other words, this is only a manner for conveniences' sake, and there is no intention of excluding hemiacetal-form compounds.

In the present invention, any of the individual tautomers, the mixture thereof, or optical isomers, the mixtures thereof, racemic modifications, and other isomers such as stereoisomers may be used for the same purpose.

Some of compounds used in the present invention can be obtained by the methods set forth in European Patent Publication 0281239A (Japanese Patent Application KOKAI No.52753/89), European Patent Publication 0690049A (Japanese Patent Application KOKAI No.48665/96) etc. As another method these compounds may be prepared according to a method as described above or a known method.

The above 15-keto-PGE compounds are useful for an endothelin antagonist.

The compounds used in the present invention may be utilized as a pharmaceutical for animal and human being, and they may usually be administered systemically or locally in accordance with ophthalmic administration, oral administration, intravenous injection (including drip infusion), subcutaneous injection, intrarectal administration and the like manner. Although the dosage varies dependent upon type, age, body weight, symptom to be treated, desired therapeutic effect, administration route, period to be treated or the like of objects such as animal or human being and the like, sufficient effect is ordinarily achieved by usually the dosage of 0.01 to 100 μg/eye in case of local administration, or the dosage of 0.0001 to 500 mg/kg in case of systemical administration in accordance with divided dose into two to four fractions per day or under sustained condition.

The ophthalmic preparations according to the present invention include ophthalmic solution or ophthalmic ointment and the like. Ophthalmic solution is prepared by either dissolving the active ingredient into sterile aqueous solution, for example, physiological saline, buffer solution and the like, or combining the former with the latter used at the time of administration. The ophthalmic ointment is prepared by mixing the active ingredient with a base.

The solid composition for oral administration used according to the present invention includes tablet, troche, sublingual tablet, capsule, pill, powder, granule and the like. In such a solid composition, one or more active ingredient(s) is (are) admixed with at least one inactive diluent such as lactose, mannitol, glucose, hydroxypropyl cellulose, microcrystalline cellulose, starch, polyvinyl pyrrolidone, magnesium aluminate metasilicate. According to a conventional procedure, a composition may contain additives other than the inactive diluent, for example, lubricant such as magnesium stearate; disintegrator such as cellulose calcium gluconate; and stabilizer, for example, etherificated cyclodextrin such as α-, β-, and γ-cyclodextrin, or dimethyl-α-, dimethyl-β-, trimethyl-β-, and hydroxypropyl-β-cyclodextrin, branched cyclodextrin such as glycosyl-, maltosyl-cyclodextrin, formilated cyclodextrin, sulfur-containing cyclodextrin, misoprotol (phonetic), and phospholipid. When any of the above described cyclodextrins is used, there is a case where a clathrate inclusion compound is formed from the cyclodextrin to increase the stability of a composition. Furthermore, there is a case when liposome is formed by utilizing phospholipid, the stability of the resulting product increases. If desired, tablet or pill may be covered or coated with a film or two or more layers made of a substance soluble in ventriculus or intestine such as saccharose, gelatin, hydroxypropyl cellulose, and hydroxypropyl methyl cellulose phthalate. Furthermore, a composition may be formed in capsule by the use of a disintegrable material such as gelatin. In case of requiring fast-acting property, a composition may be formed in sublingual tablet. As a base, glycerin, lactose and the like may be used. An example of liquid compositions for oral administration includes emulsion, solution, suspension, syrup, and elixir formulations. They may contain an inactive diluent used ordinarily such as purified water, and ethanol. Any of these compositions may further contain an additive such as wetting agent, and suspending agent; edulcorant; flavoring material, aromatic, and preservative in addition to the inactive diluents.

As another composition for oral administration, there is a spraying agent containing one or more active ingredient(s) and being formulated in accordance with a manner which itself has been well known.

An example of parenteral solutions according to the present invention includes sterile aqueous or nonaqueous solution, suspension, and emulsion. An example of media for the aqueous solution and the suspension includes distilled water for injection, physiological saline, and Ringer solution.

An example of diluent for the nonaqueous solution and the suspension includes propylene glycol, polyethylene glycol, vegetable oils such as olive oil, alcohols such as ethanol, polysorbate and the like. These compositions may further contain adjuvants such as preservative, wetting agent, emulsion, and dispersant. They are sterilized by, for example, filtration passing them through a bacteria remaining filter, incorporation of a bacteriocide, gas sterilization, or radiation sterilization. They may also be manufactured in the form of a sterile solid composition, and it is dissolved in sterile water or a sterile solvent for injection prior to the application therefor.

Another form for such compositions is suppository or vaginal suppository. These suppositories may be prepared by admixing an active ingredient with a base such as cacao butter or the like which softens at body temperature, and in this case, a nonionic surfactant having a suitable softening temperature may be added further to improve the absorption thereof.

EXAMPLE

Although the present invention will be explained in detail by the following examples of syntheses and tests, they do not limit the invention.

Synthetic Example 1

Synthesis of 16,16-difluoro-13,14-dihydro-15-keto-PGE$_1$ Methyl Ester (12)

1-1) Synthesis of (1S,5R,6R,7R)-6-hydroxymethyl-7-tetrahydropyranyloxy-2-oxabicyclo[3.3.0]octan-3-one (2)

Tetrabutyl ammonium fluoride in tetrahydrofuran (THF) (1.0M, 300 ml) was added into the solution of commercially available (−) Corey lactone (1) (protected with THP) (37.9 g) in THF, and the mixture was stirred at a room temperature for 3 hours.

The reaction solution was concentrated under a reduced pressure, and the obtained residue was subjected with a column chromatography to give the titled compound (2). Yield: 21.70 g (82.8%)

1-2) Synthesis of (1S,5R,6R,7R)-6-{(E)-4,4-difluoro-5-oxo-2-octenyl}-7-tetrahydropyranyloxy-2-oxabicyclo[3.3.0]octan-3-one (4)

Oxalyl chloride in methylene chloride (2.0M, 45.5 ml) was dissolved in methylene chloride at −78° C. under argon atmosphere, into which dimethyl sulfoxide (DMSO)(12.9 ml) was dropped with stirring for 10 minutes. Into the resultant the solution of (1S,5R,6R,7R)-6-hydroxymethyl-7-tetrahydropyranyloxy-2-oxabicyclo[3.3.0]octan-3-one (2) (11.65 g) in methylene chloride was dropped, stirred for 30 minutes, and triethylamine (56 ml) was dropped and stirred for one hour. The reaction product was treated by a usual work-up to give a crude product of aldehyde (3).

Dimethyl 3,3-difluoro-2-oxoheptylphosphonate (11.9 g) was added into a solution of thallium ethoxide (3.26 ml) in methylene chloride and stirred for one hour under argon atmosphere. The mixture was cooled to 0° C., to which the solution of aldehyde (3) prepared above in methylene chloride was added and stirred at a room temperature for 14 hours. Into the reaction solution acetic acid, celite and saturated aqueous solution of potassium iodide, and filtered. The filtrate was treated with a usual manner, and the obtained crude product was subjected to a column chromatography to give a titled compound (4). Yield: 7.787 g (44.3%)

1-3) Synthesis of (1S,5R,6R,7R)-6-(4,4-difluoro-5-oxooctyl)-7-tetrahydropyranyloxy-2-oxabicyclo[3.3.0]-octan-3-one (5)

5% Palladium-carbon (catalytic amount) was added into the solution of (1S,5R,6R,7R)-6-{(E)-4,4-difluoro-5-oxo-2-octenyl}-7-tetrahydropyranyloxy-2-oxabicyclo-[3.3.0]octan-3-one (4) (5.57 g) in ethyl acetate, and mixed at a room temperature for 7 hours under hydrogen gas atmosphere. The reaction solution was filtered, and the filtrate was concentrated under a reduced pressure to give the titled compound (5) as a crude product. Yield: 5.48 g (97.8%)

1-4) Synthesis of (1S,5R,6R,7R)-6-{4,4-difluoro-5(RS)-hydroxyoctyl}-7-tetrahydropyranyloxy-2-oxabicyclo [3.3.0]-octan-3-one (6)

Sodium borohydride (0.800 g) was added to the solution of (1S,5R,6R,7R)-6-(4,4-difluoro-5-oxo-octenyl)-7-tetrahydropyranyloxy-2-oxabicyclo[3.3.0]-octan-3-one (5) (5.48 g) in methanol at 0° C., and stirred for 10 minutes. The reaction product was treated with a usual manner, and the obtained crude product was subjected to column chromatography to give a titled compound (6). Yield: 5.46 g (99.5%)

1-5) Synthesis of 16,16-difluoro-13,14-dihydro-11-tetrahydropyranyloxy-PGF$_{2\alpha}$ methyl ester (9)

The solution of (1S,5R,6R,7R)-6-{4,4-dihydro-5(RS)-hydroxyoctyl}-7-tetrahydropyranyloxy-2-oxabicyclo [3.3.0]-octan-3-one (6) (2.579 g) in toluene was cooled to −78° C. under argon atmosphere, to which diisobutylaluminum hydride in toluene (1.5M, 9.6 ml) was added, and stirred for 30 minutes. Into the reaction solution methanol and a saturated aqueous solution of Rochelle salt were added, and treated with a usual manner to give lactol (7) as a crude product.

Solution of potassium t-butoxide in THF (1.0M, 52.84 ml) was dropped to the suspension of 4-carboxybutyl triphenylphosphine bromide (11.72 g) in THF under argon atmosphere and stirred for 20 minutes. The reaction solution was cooled to 0° C., to which the solution of lactol (7) in THF prepared above was added and stirred at a room temperature for 15 hours.

The reaction solution was treated with a usual manner to give the carboxylic acid (8) as a crude product.

1,8-Diazabicyclo[5.4.0]undec-7-ene (DBU) (4.0 ml) and methyl iodide (1.7 ml) was added into the solution of the carboxylic acid (8) in acetonitrile under argon atmosphere, and stirred at 60° C. for 3 hours. A crude product obtained by a usual manner was subjected to a column chromatography to give the titled compound (9). Yield: 2.737 g (84.5%)

1-6) Synthesis of 16,16-difluoro-13,14-dihydro-15-keto-11-tetrahydropyranyloxy-PGE$_2$ methyl ester (10)

The solution of 16,16-difluoro-13,14-dihydro-11-tetrahydropyranyloxy-PGF$_{2\alpha}$ methyl ester (9) (2.646 g) in methylene chloride was added into a solution of Collins reagent in methylene chloride, which was prepared according to a usual work-up from pyridine (26.2 ml) and chromic acid anhydride (16.18 g) at −20° C. under argon atmosphere, and stirred for 2 hours. The reaction product was further stirred at −5° C. for 9 hours. Into the reaction product ether and sodium hydrogen sulfate were added, and filtered. The filtrate was concentrated under a reduced pressure, and then subjected to a column chromatography to give the titled compound (10). Yield: 1.890 g (64.4%)

1-7) Synthesis of 16, 16-difluoro-13, 14-dihydro-15-keto-PGE$_2$ methyl ester(11)

16,16-difluoro-13,14--dihydro-15-keto-11-tetrahydropyranyloxy-PGE$_2$ methyl ester (10) (2.809 g) was dissolved in a mixed solvent of acetic acid, water and THF (3:1:1), and the mixture was stirred at 60° C. for 5 hours. The reaction solution was concentrated under a reduced pressure, and was subjected to a column chromatography to give the titled compound (11). Yield: 1.755 g (75.5%)

1-8) Synthesis of 16,16-difluoro-13,14-dihydro-15-keto-PGE$_1$ methyl ester (12)

5% Palladium-carbon (catalytic amount) was added to the solution of 16,16-difluoro-13,14-dihydro-15-keto-PGE$_2$ methyl ester (11) (1.755 g) in ethyl acetate, and stirred at a room temperature for 6 hours under hydrogen gas atmosphere. The reaction solution was filtered, and the filtrate was concentrated under a reduced pressure. The product was subjected to a column chromatography to give the titled compound (12). Yield: 1.655 g (93.8%)

$^1$H NMR (CDCl$_3$) δ 0.87(3H, t, J=7 Hz), 1.15–2.05(23H, m), 2.11~2.30 (3H, m), 2.50(1H, dd, J=7.5 and 17 Hz), 3.10–3.20 (1H, br), 3.71 (3H, s), 4.05–4.20(1H, m).

Mass(D1-E1) m/z 404 (M$^+$), 355 (M$^+$-H$_2$O-CH$_3$O), 297 (M$^+$-C$_5$H$_9$F$_2$)

Synthetic Example 2

Synthesis of 16,16-difluoro-13,14-dihydro-15-keto-PGE$_1$ (16)

2-1) Synthesis of (15RS)16,16-difluoro-13,14-dihydro-11-tetrahydropyranyloxy PGF$_{2\alpha}$ benzyl ester (13)

DBu (2.1 ml) and benzyl bromide (2.2ml) were added to the solution of carboxylic acid (8) (2.33 g) in dichloromethane (300 ml) and the mixture was stirred at room temperature for 1.5 hours. A crude product obtained by a usual work-up was purified by a silica gel column to give the benzyl ester (13). Yield: 2.522 g (96.1%)

2-2) Synthesis of 16,16-difluoro-13,14-dihydro-15-keto-11-tetrahydropyranyloxy PGE$_2$ benzyl ester (14)

Collins reagent was prepared using chromic acid anhydride (13.5 g) and pyridine (21.8 ml) in dichloromethane, to which celite (40 g) was added, and the above benzyl ester (13) (2.550 g) was oxidized at −20° C. The crude product obtained after treated by a usual work-up was purified by a silica gel to give the titled compound (14). Yield: 1.911 g (78.6%)

2-3) Synthesis of 16,16-difluoro-13,14-dihydro-15-keto-PGE$_2$ benzyl ester (15)

The PGE$_2$ benzyl ester (14) (1.550 g) was dissolved in acetic acid-THF-water (3-1-1, 50 ml), and kept at 50° C. for 4 hours. A crude product obtained by a usual work-up was purified by a silica gel column to give PGE$_2$ benzyl ester (15). Yield: 1.255 g (92.9%)

2-4) Synthesis of 16,16-difluoro-13,14-dihydro-15-keto-PGE$_1$ (16)

PGE$_2$ benzyl ester (15) (0.844 g) was subjected to a catalytic reduction using 5% palladium-carbon in ethyl acetate. The product was purified by a column to give 16,16-difluoro-13,14-dihydro-15-keto-PGE$_1$ (16). Yield: 0.404 g $^1$H NMR (CDCl$_3$) δ 0.94 (3H, t, J=7.5 Hz), 1.20–2.70 (26H, m), 4.19 (1H, m), 4.80 (2H, br).

Mass (DI-EI) m/z 390 (M$^+$), 372 (M$^+$-H$_2$O), 354 (M$^+$-2H$_2$O)

The reaction scheme is shown hereinafter:
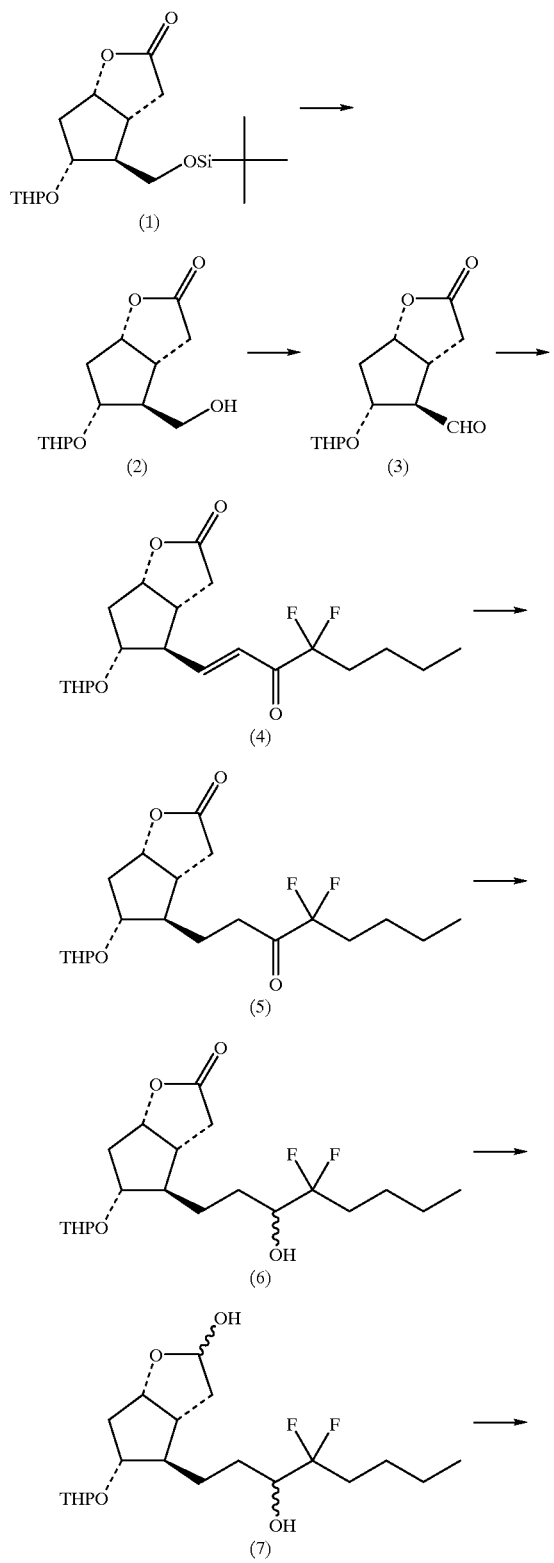
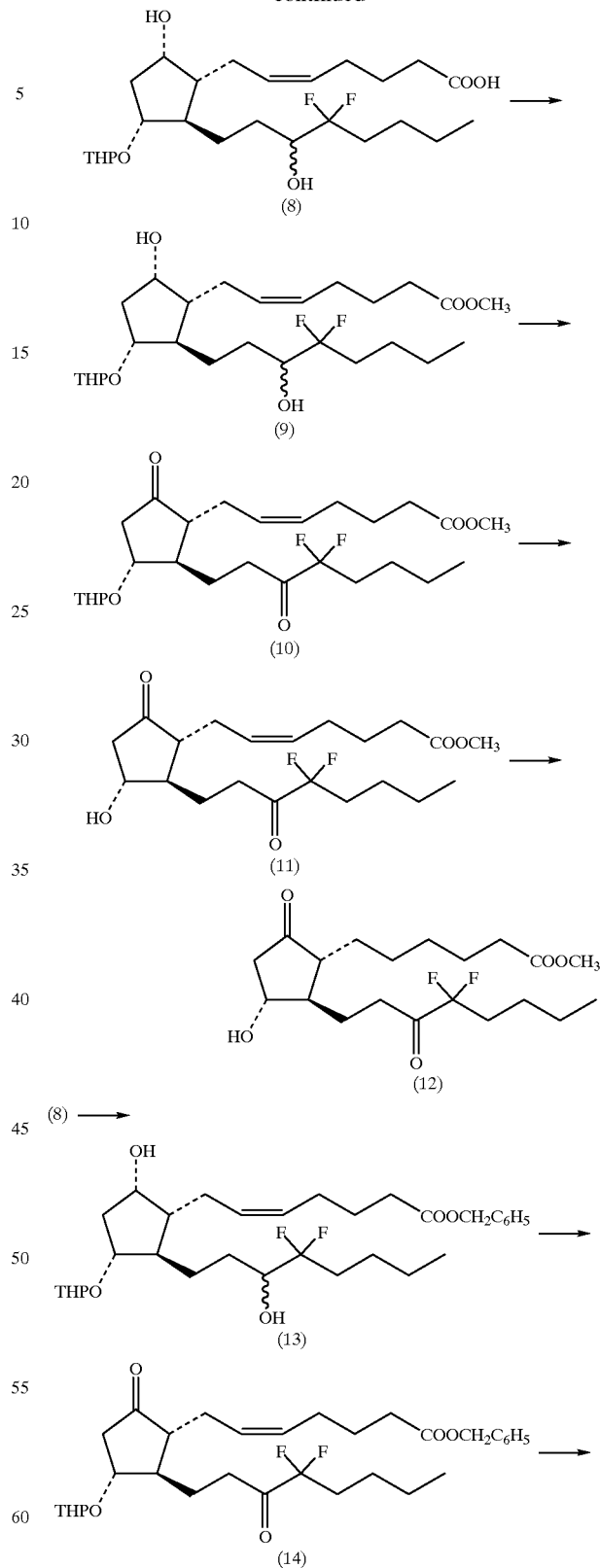

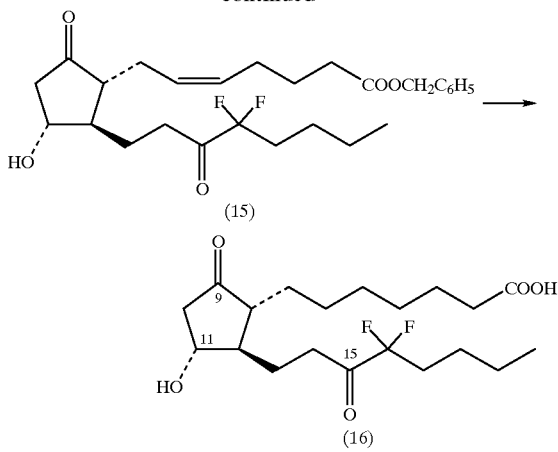

Test Example 1

Method

1. Induction of Peripheral Circulation insufficiency with Endothelin 1 in dogs:

Beagle dogs (male and female, body weight: 8.2–11.8 kg) were used for this study. After the animals were anesthetized by an intravenous administration and a subcutaneous administration of pentobarbital, the femoral artery in one of hind limbs was exposed. Catheters for the administration of endothelin-1 (referred to as ET-1 hereinafter) and for the determination of the arterial blood pressure were inserted into small branches of the femoral artery and fastened. After shaving the dorsum of the distal parts of the hind limbs, probes of a laser Doppler flowmeter (ALF21D: Advance Co, Ltd.) were placed on the cutaneous surface in order to determine the cutaneous tissue blood flow. ET-1 (Peptide Institute Inc.) was continuously infused into the femoral artery at a rate of 3 pmol/kg/min. with a syring pump (model 1100, KD, Scientific Inc.) via the catheter inserted into the branch of the femoral artery so as to induce peripheral circulation inssufficency.

2. Experimental Group

TABLE 1

| experimental group | dose ($\mu$g/0.5 ml/kg) | administration root | Model numbers (n) |
|---|---|---|---|
| Control (vehicle) | — | Intravenous | 3 |
| Test compound 1 | 0.3 | Intravenous | 3 |
| Test compound 1 | 1.0 | Intravenous | 3 |

Vehicle: physiological saline containing 0.01% polysolvate 80 and 0.5% ethanol

Test compound 1: 13,14-dihydro-15-keto-16,16-difluoro-18S-methyl-prostaglandin $E_1$ 3. Experimental Schedule:

After 30–40 minutes from the beginning of continuous infusion of ET-1 into the one side of the femoral artery, the cutaneous tissue blood flow in the dorsum of the distal part of the hind limb to which ET-1 was injected was reduced. After it was confirmed that the cutaneous tissue blood flow decreased and reached a steady level, the vehicle or the test compound was administrated for 2 minutes through the catheter placed in the duodenum. The cutaneous tissue blood flow in both dorsums of distal part of the hind limbs and the mean blood pressure were determined and recorded for 40 minutes after the administration.

Results

The results of the measurement of the cutaneous tissue blood flow in the dorsum of the distal part of the hind limb (mean±S.D. ml/100 g/min) are shown in Table 2. The time (minutes) represents a time after the administration of vehicle or the test compound. Pre-value 1 is a value just before starting of the continuous infusion of ET-1, and Pre-value 2 means a value just before the administration of the vehicle or test compounds.

TABLE 2

| experimental group | dose ($\mu$g/kg, i.v.) | model numbers (n) | pre-value | | Time (min.) | | | |
|---|---|---|---|---|---|---|---|---|
| | | | 1 | 2 | 10 | 15 | 25 | 35 |
| control (vehicle) | — | 3 | 5.8 ± 1.0 | 3.5 ± 0.1 | 3.6 ± 0.1 | 3.5 ± 0.2 | 3.5 ± 0.3 | 3.6 ± 0.2 |
| test compound 1 | 0.3 | 3 | 5.9 ± 1.0 | 3.6 ± 0.4 | 3.7 ± 0.4 | 3.7 ± 0.4 | 3.7 ± 0.5 | 3.7 ± 0.4 |
| test compound 1 | 1.0 | 3 | 5.9 ± 1.0 | 3.6 ± 0.3 | 4.2* ± 0.1 | 4.2* ± 0.1 | 4.1 ± 0.1 | 3.9 ± 0.1 |

* $p < 0.05$ compared with the control by Dunnett test

As clearly shown in Table 2 the cutaneous tissue blood flow in the dorsum of the distal part of the hind limb to which ET-1 was administrated was reduced by about 40% in comparison with that before the administration of ET-1 by the continuous infusion of ET-1 into the femoral artery. The test compound 1 recovered dose dependently the cutaneous tissue blood flow which was decreased with ET-1. Especially in the 1.0 $\mu$g/kg administration group, a significant increase in the cutaneous tissue blood flow was observed at 10 or 15 minutes after the administration compared with the control group.

No influence by the administration of ET-1 was observed in the cutaneous tissue blood flow of the hind limb to which ET-1 was not administrated. Further, no influence by intravenous administration of the test compound observed.

Further, any influence on the arterial blood pressure by the administration of ET-1 and the test compound was not observed.

The above results show that the endothelin antagonist of the present invention has a significant antagonistic activity against circulation disorder induced with endothelin.

Availability in the Industries

The compounds used in the present invention are useful as an endothelin antagonist. Therefore, they are expected for a cure or prevention of hypertension, Buerger disease, asthma, eyegrounds diseases and the like.

What is claimed is:

1. A method for treatment of a disease caused by an excessive production of endothelin, which comprises administering to a subject in need of such treatment an effective amount of a 15-keto-prostaglandin E compound excluding compounds in which the number of backbone carbon atoms in α-chain is 8 or more.

2. A method of claim 1, in which the 15-keto-prostaglandin E compound is a compound represented by following formula (I):

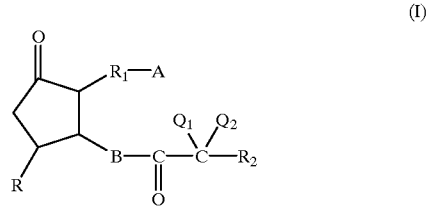

wherein R is a hydrogen atom, a hydroxyl group, a hydroxy lower alkyl group or a lower alkyl group;

A is —CH$_2$OH, —COCH$_2$OH, —COOH, or functional derivatives thereof;

B is —CH$_2$—CH$_2$—, —CH=CH— or —C—C—, $Q_1$ and $Q_2$ are a hydrogen atom, a halogen atom or a lower alkyl group;

$R_1$ is a bivalent saturated or unsaturated $C_{2-6}$ hydrocarbon residue which is unsubstituted or substituted with halogen, oxo or aryl, wherein said aryl of said $R_1$ is an aromatic hydrocarbon ring or a monocyclic heterocyclic group;

$R_2$ is a saturated or unsaturated, lower to medium aliphatic hydrocarbon residue which is unsubstituted or substituted with halogen, oxo, hydroxy, lower alkoxy, lower alkanoyloxy, lower cycloalkyl, aryl or aryloxy; a lower cycloalkyl group; an aryl group or an aryloxy group, wherein said aryl and aryl of aryloxy in said $R_2$ in the compound of formula (I) is an aromatic hydrocarbon ring or a monocyclic heterocyclic group.

3. A method of claim 1, in which the 15-keto-prostaglandin E compound is a 15-keto-16-mono or dihalogen-prostaglandin E compound.

4. A method of claim 1, in which the 15-keto-prostaglandin E compound is a 13,14-dihydro-15-keto-prostaglandin E compound.

5. A method of claim 1, in which the 15-keto-prostaglandin E compound is a 13,14-dihydro-15-keto-16-mono or dihalogen-prostaglandin E compound.

6. A method of claim 1, in which the 15-keto-prostaglandin E compound is a 15-keto-16-mono or difluoro-prostaglandin E compound.

7. A method of claim 1, in which the 15-keto-prostaglandin E compound is a 13,14-dihydro-15-keto-16-mono or difluoro-prostaglandin E compound.

8. A method of claim 1, in which the 15-keto-prostaglandin E compound is a 13,14-dihydro-15-keto-16-mono or difluoro-18-methyl-prostaglandin E compound.

9. A method of claim 1, in which the 15-keto-prostaglandin E compound is a 13,14-dihydro-15-keto-16-mono or difluoro-18-methyl-prostaglandin E1 compound.

10. A method of any one of claims 1, 2, 3, 4, 5, 6, 7, 8, or 9, in which the administration is carried out by a method selected from the group consisting of an eye drop, oral administration, intravenous administration, hypodermic injection and intrarectal administration.

11. A method of any one of claims 1, 2, 3, 4, 5, 6, 7, 8, or 9, in which the 15-keto-prostaglandin E compound is administered by eye drop in a dose of 0.01 to 100 μg/eye.

12. A method of claim 1, in which the 15-keto-prostaglandin is systemically administered in a dose of 0.0001 to 500 mg by 2 to 4 aliquots a day.

13. A method of claim 1, in which the disease caused by the excessive production of the endothelin is hypertension, pulmonary hypertension, Buerger's disease, Raynaud disease, asthma, eyegrounds diseases, diabetes, arterial sclerosis, renal failure, cardiac infarction, angina pectoris, cerebrovascular contraction, cerebral infarction or a complication thereof.

14. A method of claim 1, in which the disease caused by the excessive production of the endothelin is a circulation disorder.

* * * * *